(12) United States Patent
Eda

(10) Patent No.: US 11,642,102 B2
(45) Date of Patent: May 9, 2023

(54) ULTRASOUND DIAGNOSTIC DEVICE

(71) Applicant: Hitachi, Ltd., Tokyo (JP)

(72) Inventor: Masato Eda, Tokyo (JP)

(73) Assignee: FUJIFILM Healthcare Corporation, Chiba (JP)

( * ) Notice: Subject to any disclaimer, the term of this patent is extended or adjusted under 35 U.S.C. 154(b) by 133 days.

(21) Appl. No.: 17/192,046

(22) Filed: Mar. 4, 2021

(65) Prior Publication Data

US 2021/0344180 A1 Nov. 4, 2021

(30) Foreign Application Priority Data

Apr. 30, 2020 (JP) .............................. JP2020-080330

(51) Int. Cl.
| | |
|---|---|
| A61B 8/00 | (2006.01) |
| B65H 75/44 | (2006.01) |
| H01R 13/72 | (2006.01) |
| H02G 3/04 | (2006.01) |

(52) U.S. Cl.
CPC ............ *A61B 8/44* (2013.01); *B65H 75/4476* (2013.01); *H01R 13/72* (2013.01); *B65H 75/4402* (2013.01); *H02G 3/0456* (2013.01)

(58) Field of Classification Search
CPC ....... A61B 8/4405; A61B 8/4444; A61B 8/44; H02G 11/02; H02G 3/0456; B65H 75/4476; B65H 75/362; B65H 75/4402; H01R 13/72; H01R 2201/12; H01R 13/5213
USPC ........................................................ 242/129
See application file for complete search history.

(56) References Cited

U.S. PATENT DOCUMENTS

| | | | | |
|---|---|---|---|---|
| 2,763,707 A | * | 9/1956 | Soderberg | H02G 11/02 174/50 |
| 3,337,682 A | * | 8/1967 | Swett | H02G 11/02 242/388 |
| 4,721,268 A | * | 1/1988 | Lerner | H02G 11/02 242/129 |
| 4,858,846 A | * | 8/1989 | McDonald | H01R 13/72 242/129 |
| 4,944,694 A | * | 7/1990 | Dorn | H01R 13/72 439/501 |
| 5,615,682 A | * | 4/1997 | Stratz, Sr. | A61B 8/4405 600/459 |
| 5,673,696 A | * | 10/1997 | Bidwell | G10K 11/004 600/437 |
| 5,924,892 A | * | 7/1999 | Ferracina | H01R 13/72 439/535 |
| 6,329,597 B1 | * | 12/2001 | Kaloustian | H02G 11/02 174/67 |

(Continued)

FOREIGN PATENT DOCUMENTS

| | | |
|---|---|---|
| JP | 2011-036302 A | 2/2011 |
| JP | 2014-213171 A | 11/2014 |

*Primary Examiner* — Jonathan Liu
*Assistant Examiner* — Taylor Morris
(74) *Attorney, Agent, or Firm* — Mattingly & Malur, PC (57) ABSTRACT

A cable container is provided on a right side surface or a left side surface of a device body of an ultrasound diagnostic device. The cable container is configured to include a container body having an opening that opens upward. An upper end of a front side wall of the container body has a notch that serves as a passage through which a probe cable extends from the inside of the container body toward the outside of the container body.

8 Claims, 10 Drawing Sheets

(56) References Cited

U.S. PATENT DOCUMENTS

| | | | | |
|---|---|---|---|---|
| 7,038,126 B2* | 5/2006 | Solet | ............... | H02G 11/02 |
| | | | | 361/600 |
| 7,098,406 B1* | 8/2006 | Hammonds | ............ | B65H 75/06 |
| | | | | 242/388 |
| 7,247,798 B2* | 7/2007 | Pagoto | ............... | H02G 11/02 |
| | | | | 174/138 E |
| 8,746,606 B1* | 6/2014 | Murray | ............... | B65H 75/4473 |
| | | | | 242/129 |
| 9,775,258 B1* | 9/2017 | Sandefer | ............... | H05K 5/0221 |
| 10,117,638 B2* | 11/2018 | Stankard | ............... | H05K 5/00 |
| 10,912,477 B1* | 2/2021 | Soleyman | ............ | H01B 7/0045 |
| 2001/0007298 A1* | 7/2001 | Glass | ............... | B65H 75/4476 |
| | | | | 242/388.6 |
| 2008/0146922 A1* | 6/2008 | Steins | ............... | A61B 8/546 |
| | | | | 600/437 |
| 2010/0270191 A1* | 10/2010 | Bub | ............... | H02G 3/00 |
| | | | | 206/320 |
| 2016/0114066 A1* | 4/2016 | Lichtblau | ............... | A61L 2/10 |
| | | | | 250/455.11 |
| 2017/0006720 A1* | 1/2017 | Palmer | ............... | H01R 13/72 |
| 2019/0380681 A1* | 12/2019 | Meurer | ............... | A61B 8/4427 |
| 2020/0315573 A1* | 10/2020 | Kang | ............... | A61B 8/40 |
| 2020/0367857 A1* | 11/2020 | Teraishi | ............... | A61B 8/4405 |
| 2022/0240894 A1* | 8/2022 | Stalter | ............... | A61B 8/4411 |

\* cited by examiner

ULTRASOUND DIAGNOSTIC DEVICE

CROSS REFERENCE TO RELATED APPLICATION

This application claims priority to Japanese Patent Application No. 2020-080330 filed on Apr. 30, 2020, which is incorporated herein by reference in its entirety including the specification, claims, drawings, and abstract.

TECHNICAL FIELD

The present description discloses an ultrasound diagnostic device, and in particular, an ultrasound diagnostic device in which a device body and an ultrasound probe are connected by a probe cable.

BACKGROUND

An ultrasound diagnostic device is configured to include a device body for performing, for example, ultrasound imaging processing, and an ultrasound probe for transmitting and receiving ultrasound waves to and from a subject. Although, in recent years, ultrasound diagnostic devices that wirelessly connect the device body and the ultrasound probe have been proposed, there are also many ultrasound diagnostic devices that connect the device body and the ultrasonic probe by wire; that is, by a probe cable.

An ultrasound diagnostic device may be used in various situations, and thus, the distance between the device body and the subject during use may vary. Accordingly, the probe cable is generally designed to have a relatively long length so that the ultrasound probe can reach the subject positioned relatively far from the device body.

The long length of the probe cable sometimes makes the cable difficult to handle. Also, in terms of hygiene, it is desirable to prevent the probe cable from directly contacting the floor surface or the operator (for example, a doctor). In light of this, there has been proposed an ultrasonic diagnostic device that enables use of an ultrasound probe while accommodating a probe cable. For example, JP 2011-36302 A discloses an ultrasound diagnostic device provided with a storage portion for accommodating a probe cable. The storage portion has a container that opens upward, a roller, and a motor for driving the roller. The storage portion is structured to draw the probe cable abutting against the roller into the container by driving the motor.

CITATION LIST

Patent Literature

With the structure in which a motor or the like is used, such as that disclosed in JP 2011-36302 A, it is possible to use the ultrasound probe while accommodating the probe cable. However, adoption of such a structure increases the number of parts of the ultrasound diagnostic device, leading to the problems of a rise in cost and an increase in weight and volume of the ultrasound diagnostic device, for example.

An object of the ultrasound diagnostic device disclosed herein is to enable an ultrasound probe to be used appropriately while accommodating the excess length of a probe cable in a cable container by means of a simple structure.

SUMMARY

An ultrasound diagnostic device according to the present disclosure includes a cable container provided on either one of a right side surface and a left side surface of a device body, for accommodating a probe cable connecting an ultrasound probe and a probe connector, and in this device, the ultrasound probe transmits and receives ultrasound waves to and from a subject, and the probe connector is connected to a front side surface of the device body. The cable container has a container body having an opening that opens upward, and a notch in an upper end of a front side wall of the container body, for passing the probe cable therethrough.

According to the ultrasound diagnostic device disclosed herein, with a simple structure, it is possible to use an ultrasound probe appropriately while accommodating the excess length of a probe cable in a cable container.

BRIEF DESCRIPTION OF DRAWINGS

Embodiments of the present disclosure will be described based on the following figures, wherein.

DESCRIPTION OF EMBODIMENTS

Figure 1:
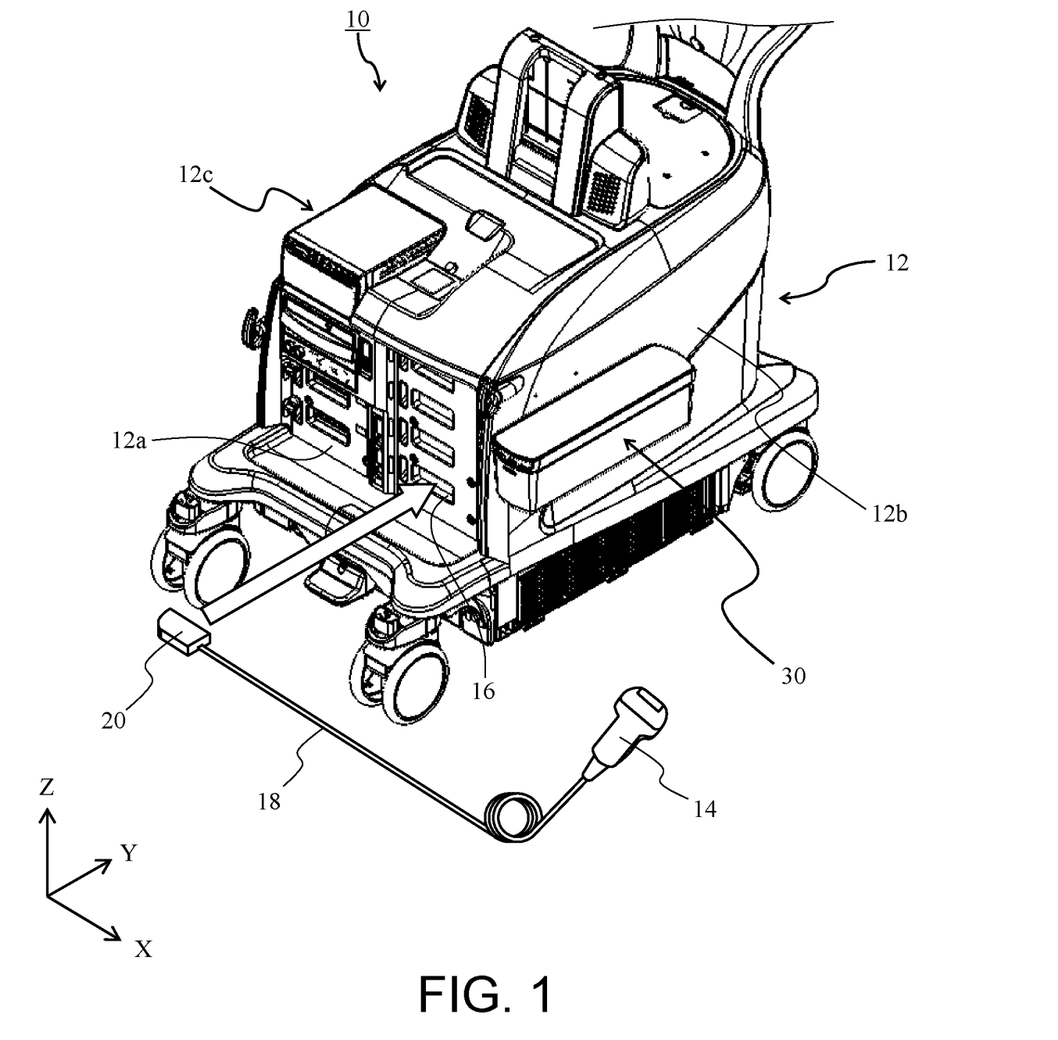
FIG. 1 is an external perspective view of an ultrasound diagnostic device according to the present embodiment.

FIG. 1 is an external perspective view of an ultrasound diagnostic device 10 according to the present embodiment. The ultrasound diagnostic device 10 is configured to include a device body 12 and an ultrasound probe 14. In FIG. 1, the X axis represents the width direction (right-and-left direction) of the device body 12. The Y direction represents the depth direction (front-and-rear direction) of the device body 12. The Z direction represents the height direction (up-and-down direction) of the device body 12.

The device body 12 transmits transmission signals to the ultrasound probe 14 to cause it to transmit ultrasound waves to a subject. The device body 12 also performs ultrasound imaging processing based on signals received from the ultrasound probe 14. The device body 12 may include a display (not illustrated in FIG. 1) for displaying, for example, an ultrasound image that has been formed. The device body 12 has, on its front side surface 12a, connectors 16 to which a probe connector 20 described below is connected.

The ultrasound probe 14 has a vibrator array composed of a plurality of vibrator elements and transmits and receives ultrasound waves to and from the subject through the vibrator array. A probe cable 18 extends from the ultrasound probe 14. The probe cable 18 is a cable for connecting the ultrasound probe 14 and a probe connector 20. The probe cable 18 includes therein a number of signal lines for communicating signals between the device body 12 and the vibrator array. The probe cable 18 is relatively long (about 2 m) so that the ultrasound probe 14 can transmit and receive ultrasound waves to and from the subject appropriately even when the device body 12 and the subject are away from each other. When the probe connector 20 is connected to the connector 16 provided on the front side surface 12a of the device body 12, the device body 12 and the ultrasound probe 14 are connected to each other physically and electrically. Although FIG. 1 illustrates only one ultrasound probe 14, the device body 12 has a plurality of connectors 16, and a plurality of ultrasound probes 14 may thus be connected to them at the same time.

The ultrasound diagnostic device 10 also has a cable container 30 for accommodating the probe cable 18, as illustrated in FIG. 1. The cable container 30 is provided on either one of a right side surface 12b and a left side surface 12c of the device body 12. As described below, the cable container 30 has a structure that can be attached to both the right side surface 12b and the left side surface 12c. The cable container 30 is detachably attached to the device body 12.

As illustrated in FIG. 1, the cable container 30 has a generally rectangular parallelepiped shape as a whole. Specifically, it has a rectangular parallelepiped shape elongated in the front-and-rear direction in its attached state. In the present embodiment, the cable container 30 is configured to include a container body and a lid, and FIG. 1 illustrates the container body to which the lid is attached.

Figure 2:
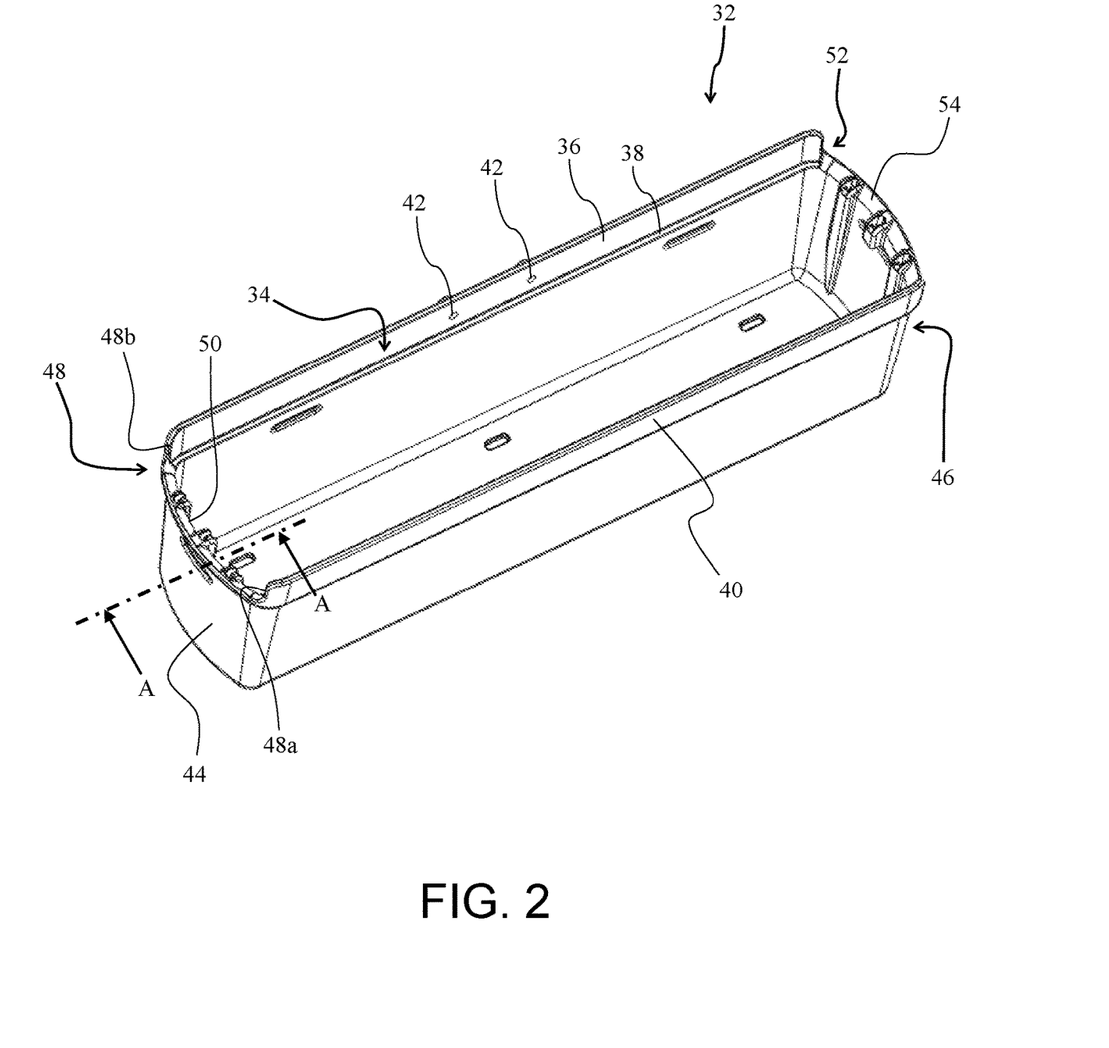
FIG. 2 is a perspective view of a container body according to the present embodiment.

FIG. 2 is a perspective view of a container body 32 (from which the lid is removed) of the cable container 30. In the following description, the terms "front", "rear", "left", "right", "up", and "down" respectively mean front, rear, left, right, up, and down on the assumption that the cable container 30 is attached to the right side surface 12b of the device body 12.

The container body 32 is made of a resin, such as plastic. The container body 32 has a generally rectangular parallelepiped shape elongated in the front-and-rear direction and has an opening 34 that opens upward. The inside of the container body 32 (space surrounded by the front, rear, left, and right walls) serves as a container chamber in which the probe cable 18 is accommodated. A left wall upper portion 36 of the container body 32 protrudes to the left side with respect to a left wall lower portion which is lower than the upper portion 36, and an upper side surface of the left wall lower portion forms a shoulder portion 38. Similarly, a right wall upper portion 40 of the container body 32 protrudes to the right side with respect to a right wall lower portion which is lower than the upper portion 40, and an upper side surface of the right wall lower portion forms a shoulder portion (not illustrated).

The left wall upper portion 36 of the container body 32 has a plurality of screw insertion holes 42 formed so as to be aligned in the longitudinal direction of the container body 32. Each of the right side surface 12b and the left side surface 12c of the device body 12 (see FIG. 1) has a plurality of screw holes aligned in the front-and-rear direction, and when screws inserted through the screw insertion hole 42 are engaged with the screw holes, the container body 32 is attached to the device body 12. Therefore, if the container body 32 is attached to the right side surface 12b, a front side wall 44 of the container body 32 is located on the front side, and a rear side wall 46 is located on the rear side. Meanwhile, if the container body 32 is attached to the left side surface 12c, the front side wall 44 of the container body 32 is located on the rear side, and the rear side wall 46 is located on the front side.

An upper end of the front side wall 44 has a notch 48. In other words, the front side wall 44 has a shape in which a portion of an upper end of the front side wall 44 is cut off. A right side end portion of the notch 48 will be referred to as a notch right end 48a, and a left side end portion of the notch 48 will be referred to as a notch left end 48b. In the present embodiment, the upper end of front side wall 44 is cut off entirely in the width direction (right-and-left direction), and the notch 48 extends across the front side wall 44 in the width direction. Thus, the notch right end 48a is a front side end of the right wall upper portion 40, and the notch left end 48b is a front side end of the left wall upper portion 36. However, this is not limiting, and the notch 48 may be provided in at least a part of the front side wall 44 in the width direction. The notch 48 serves as a passage through which the probe cable 18 extends from the inside of the container body 32 (container chamber for the probe cable 18) to the outside of the container body 32 (specifically, toward the probe connector 20 or the ultrasound probe 14).

Figure 3:
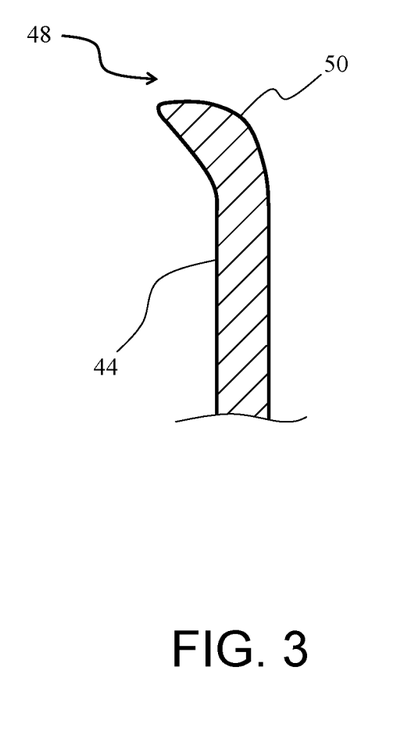
FIG. 3 is a cross-sectional view of a front side surface of the container body.

It is desirable that an inside corner of the notch 48 (inner side of the container body 32) be chamfered. This prevents or reduces damage to the probe cable 18 when the probe cable 18 abuts against the notch 48. FIG. 3 is a cross-sectional view of the front side wall 44 viewed from the A-A direction in FIG. 2. As illustrated in FIG. 3, in the present embodiment, the inside corner of the notch 48 has a gentle slope 50. The upper portion of the front side wall 44 (portion directly under the notch 48) is warped outward (toward the front side), which prevents the front side wall 44 from being thinned due to the slope 50. Reduction in strength of the upper portion of the front side wall 44 is thus prevented.

An operator of the ultrasound diagnostic device 10, such as, for example, a doctor, can collect and put the excess length of the probe cable 18 into the container body 32 through the opening 34. The probe cable 18 accommodated in the container body 32 extends from the inside to the outside of the container body 32 through the notch 48. By passing the probe cable 18 through the notch 48, the probe cable 18 can be maintained so as to extend forward from the inside of the container body 32. Specifically, even when, for example, the probe cable 18 is pulled to the right or left side due to movement of the ultrasound probe 14 in the right or left direction, the probe cable 18 (portion passing through the notch 48) abuts against the notch right end 48a or the notch left end 48b and is prevented from being moved further in the right or left direction. In this way, the appearance of the probe cable 18 extending from the container body 32 becomes tidy, and the probe cable 18 can be less likely to tangle, as it always extends in one direction. These effects become apparent particularly when a plurality of probe cables 18 are accommodated in the container body 32. In addition, because the probe connector 20 is connected to the front side surface 12a of the device body 12, and the subject is often positioned in front of the device body 12, it is possible to reduce the wiring length of the probe cable 18 outside the container body 32 by providing the notch 48, which is a passage for the probe cable 18, on the front side of the container body 32. Furthermore, by providing the notch 48 in the upper end of the front side wall 44, a position at which the probe cable 18 exits from the inside of the container body 32 becomes away from the floor surface, and the probe cable 18 extending from the notch 48 becomes less likely to contact the floor surface.

As described above, if the container body 32 is attached to the left side surface 12c; specifically, if the screws are inserted through the plurality of screw insertion holes 42 formed in the left wall upper portion 36 of the container body 32 and engaged into screw holes provided in the left side surface 12c (see FIG. 1) of the device body 12, the rear side wall 46 is located on the front side. In this case again, like the front side wall 44, it is desirable to provide a notch 52 in an upper end of the rear side wall 46, for passing the probe cable 18 therethrough, so that the probe cable 18 accommodated in the container body 32 can extend forward. It is also desirable that an inside corner of the notch 52 (inner side of the container body 32) be chamfered (a slope 54 in the present embodiment). The details and functions of the notch 52 are similar to those of the notch 48, and their description will thus be omitted.

Desirably, the container body 32 has a hook portion therein for hooking the probe cable 18. By hooking the probe cable 18 in the hook portion inside the container body 32, the wiring route of the probe cable 18 in the container body 32 can be defined, thereby preventing or reducing tangling of the probe cable 18. Also, by hooking the probe cable 18 in the hook portion, the probe cable 18 accommodated in the container body 32 can be prevented from falling off from the container body 32 even when the probe cable 18 is pulled due to movement of the ultrasound probe 14, for example.

Although the hook portion may be achieved by means of members having various shapes, two typical examples of the hook portion will be described below.

Figure 4:
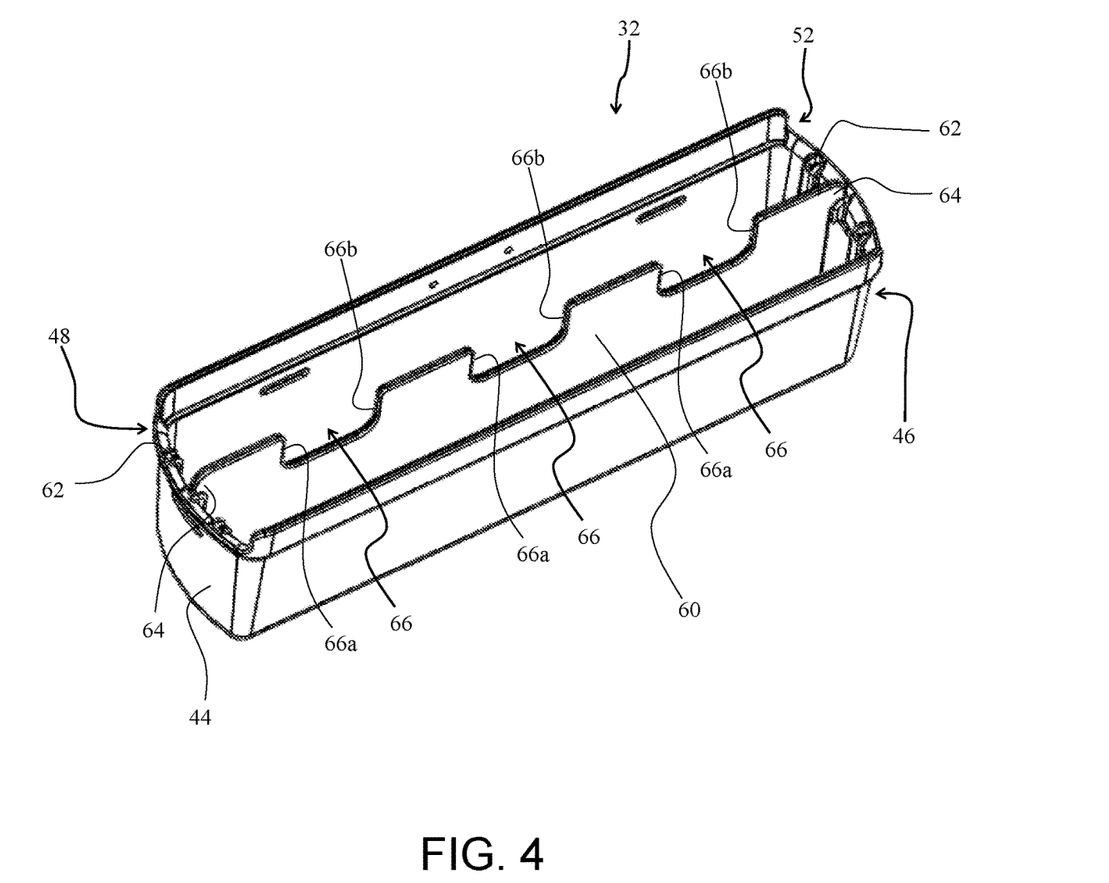
FIG. 4 is a perspective view illustrating a partition.

FIG. 4 is a perspective view illustrating a partition 60 attached in the container body 32 for functioning as the hook portion. Partition engagement portions 62 are formed on the inner surfaces of the upper portions of the front side wall 44 and the rear side wall 46 (directly under the notches 48 and 52) of the container body 32. The partition engagement portion 62 is a recess having a width (length in the right-and-left direction) which is about the thickness of the partition 60. One partition engagement portion 62 may be provided for each of the front side wall 44 and the rear side wall 46; that is, it may be case that only a pair of partition engagement portions 62 is provided. Alternatively, a plurality of partition engagement portions 62 may be arranged in the right-and-left direction to provide a plurality of pairs of partition engagement portions 62. In the present embodiment, three pairs of partition engagement portions 62 are arranged as illustrated in FIG. 4 (or FIG. 2).

The partition 60 is a plate-like member having a generally rectangular shape. Its length in the longitudinal direction is almost the same as the length of the interior space of the container body 32 in the longitudinal direction, and its length in the short direction is almost the same as the height of the interior space of the container body 32 (length in the up-and-down direction). The partition 60 has flange portions 64 protruding outward from its short sides along the longitudinal direction. When the flange portions 64 are engaged into the partition engagement portions 62, the partition 60 is detachably attached to the container body 32. In the attached state, the partition 60 stands substantially vertically on the bottom surface of the container body 32.

In the attached state, the long side of the partition 60 located on the upper side has one or more notches 66. In the present embodiment, it has three notches 66. The notches 66 serve as the hook portions for hooking the probe cable 18. Specifically, when the container body 32 is attached to the right side surface 12b of the device body 12, the probe cable 18 from the probe connector 20 side enters the inside of the container body 32 through the notch 48 and is hooked in the notch 66 (specifically, a front side end 66a of the notch 66). The probe cable 18 then extends to the outside of the container body 32 (toward the ultrasound probe 14) through the notch 48 again. Inevitably, the probe cable 18 enters the inside of the container body 32 through a portion of the notch 48 located on one side (for example, the left side) of the partition 60 and then exits to the outside of the container body 32 through a portion of the notch 48 located on the other side (for example, the right side) of the partition 60. As such, the partition 60 also functions to define, in the notch 48, an inlet and an outlet for the probe cable 18.

Providing a plurality of notches 66 in the partition 60 allows the operator to select the notch 66 for hooking the probe cable 18 according to the length of the excess length of the probe cable 18. For example, it is possible to hook the probe cable 18 in the notch 66 on the front side when the excess length is short, in the notch 66 on the rear side when the excess length is long, or in the notch 66 in the center when the excess length is intermediate between the above two cases.

The notches 66 of the partition 60 also function as the hook portions when the container body 32 is attached to the left side surface 12c of the device body 12. Specifically, the probe cable 18 enters the inside of the container body 32 through the notch 52 in the rear side wall 46 and is hooked in the notch 66 (specifically, a rear side end 66b of the notch 66). The probe cable 18 then extends to the outside of the container body 32 through the notch 52 again.

If a plurality of pairs of partition engagement portions 62 are provided, it is possible to select a position to which the partition 60 is attached. This allows adjustment of a position at which the probe cable 18 is hooked in the right-and-left direction.

The container body 32 can also be used as a container for accommodating a variety of articles, in addition to the probe cable 18. In that case, the partition 60 is literally used as a partition for dividing the interior space of the container body 32. If a plurality of pairs of partition engagement portions 62 are provided, it is possible to change a position to which the partition 60 is attached according to, for example, the size of an article to be accommodated in the container body 32.

Figure 5:
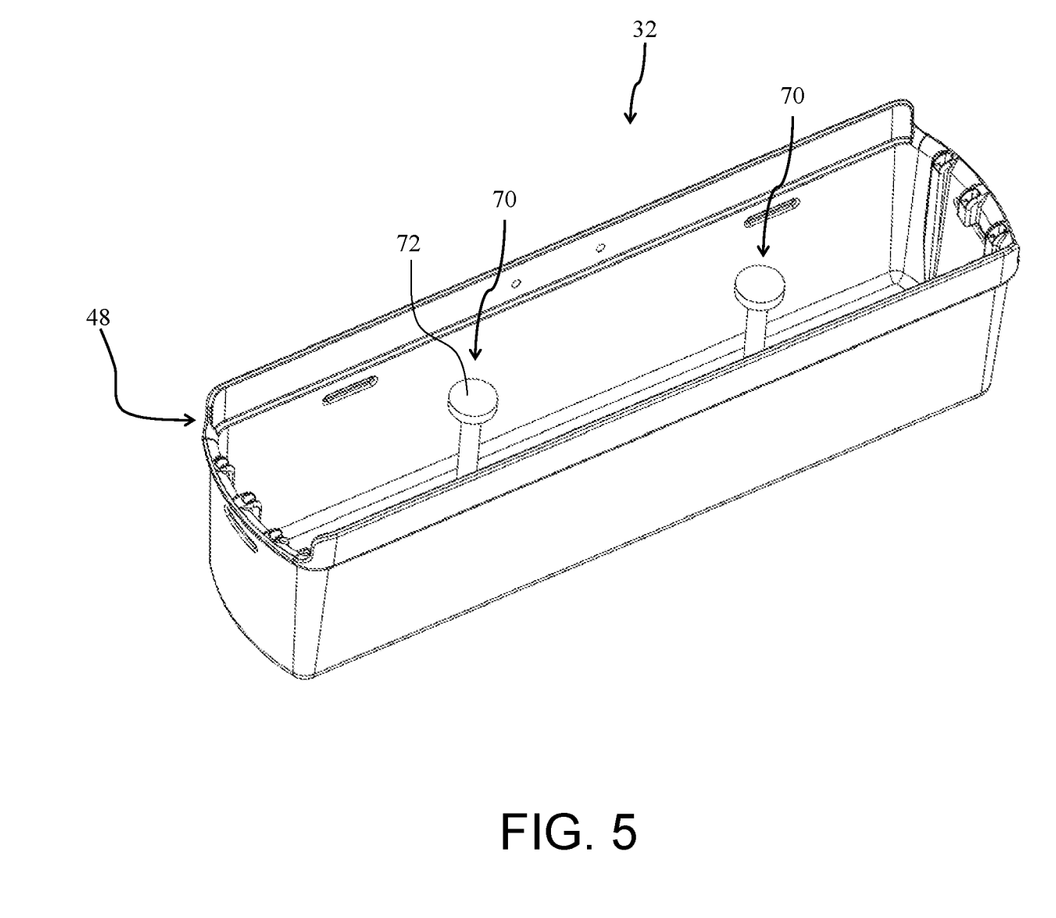
FIG. 5 is a perspective view illustrating cable hook bars.

FIG. 5 is a perspective view illustrating, as the hook portions, hook bars 70 attached in the container body 32. The hook bar 70 is a bar-like member and is almost as long as the height of the interior space of the container body 32 (length in the up-and-down direction). The hook bar 70 is attached to the bottom surface of the container body 32 so as to stand and extend in the up-and-down direction. A plurality of hook bars 70 may be aligned in the front-and-rear direction. In an example in FIG. 5, two hook bars 70 are provided.

When the container body 32 is attached to the right side surface 12b of the device body 12, the probe cable 18 that has entered the inside of the container body 32 through the notch 48 is hooked in the hook 70 and extends to the outside of the container body 32 through the notch 48 again. In order to prevent the probe cable 18, which is hooked, from falling off from an upper portion of the hook bar 70, desirably, the upper portion of the hook bar 70 is provided with a flange portion 72 extending in the horizontal direction.

Providing a plurality of hook bars 70 allows the operator to select the hook bar 70 for hooking the probe cable 18 according to the length of the excess length of the probe cable 18.

The hook bar 70 also functions as the hook portion for hooking the probe cable 18 when the container body 32 is attached to the left side surface 12c of the device body 12.

Figure 6:
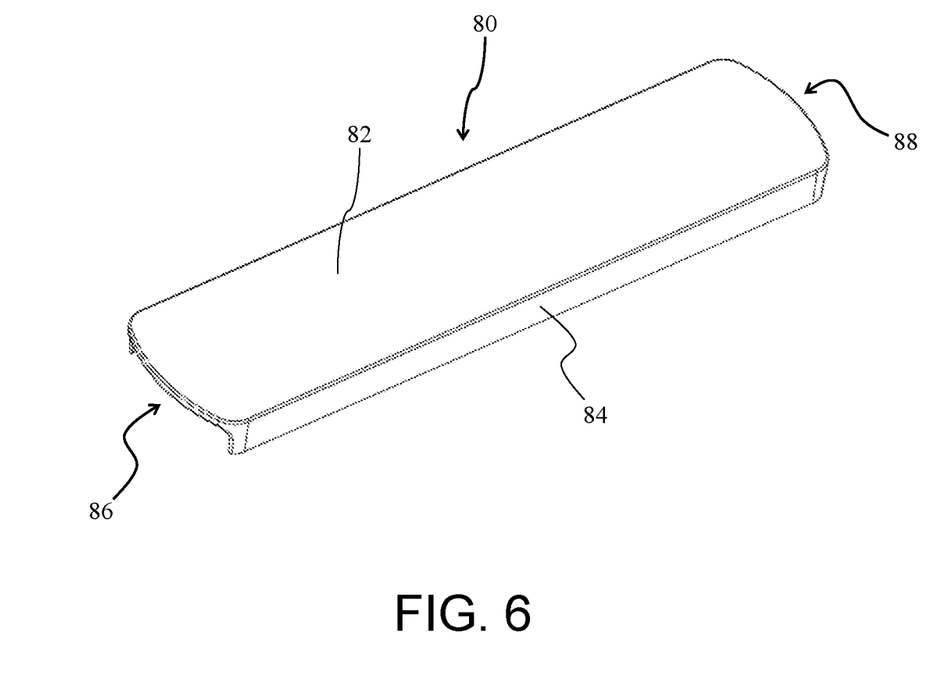
FIG. 6 is a perspective view illustrating a lid to be attached to the container body.

FIG. 6 is a perspective view illustrating a lid 80 to be attached to the container body 32. The lid 80 blocks the opening 34 of the container body 32 and is detachably attached to the container body 32. Like the container body 32, the lid 80 is made of a resin, such as plastic. The lid 80 may be transparent or translucent so that the operator can see the inside of the container body 32 even when the lid 80 is attached to the container body 32. Alternatively, the lid 80 may be opaque to make the inside of the container body 32 invisible for the sake of aesthetics.

The lid 80 is configured to include a flat plate portion 82 extending in the horizontal plane, and side plate portions 84 extending from the lower side surface of the flat plate portion 82 downward, along an edge portion of the flat plate portion 82. The flat plate portion 82 has a shape corresponding to the shape of the opening 34 of the container body 32; that is, it has a generally rectangular shape extending in the front-and-rear direction, as viewed in a plan view. The side plate portion 84 on the front side has a notch 86. In other words, a portion of the side plate portion 84 on the front side is cut off. The width of the notch 86 (length in the right-and-left direction) is the same as that of the notch 48 in the front side wall 44 of the container body 32. A similar notch 88 is also provided in the side plate portion 84 on the rear side.

When the lid 80 is placed on the container body 32 (on the opening 34), and the bottom surfaces of the side plate portions 84 on the right and left sides abut against the shoulder portions 38 (see FIG. 2) of the container body 32, the lid 80 is attached to the container body 32. In the attached state, the lid 80 forms an upper side surface of the cable container 30.

Although, as described above, the lid 80 is detachable, a lock mechanism for preventing the lid 80 from moving upward and easily coming off may be provided. For example, it is possible to provide protrusions (or ridges) on the upper ends of the inner surfaces of the left wall upper portion 36 and the right wall upper portion 40 (see FIG. 2) and prevent the lid 80 from moving upward by means of the protrusions. The lid 80 may also be sandwiched between the left wall upper portion 36 and the right wall upper portion 40 by adjusting the inside dimension between the left wall upper portion 36 and the right wall upper portion 40 (see FIG. 2) of the container body 32 and the outside dimension between the side plate portion 84 on the right side and the side plate portion 84 on the left side of the lid 80 (see FIG. 6).

Figure 7:
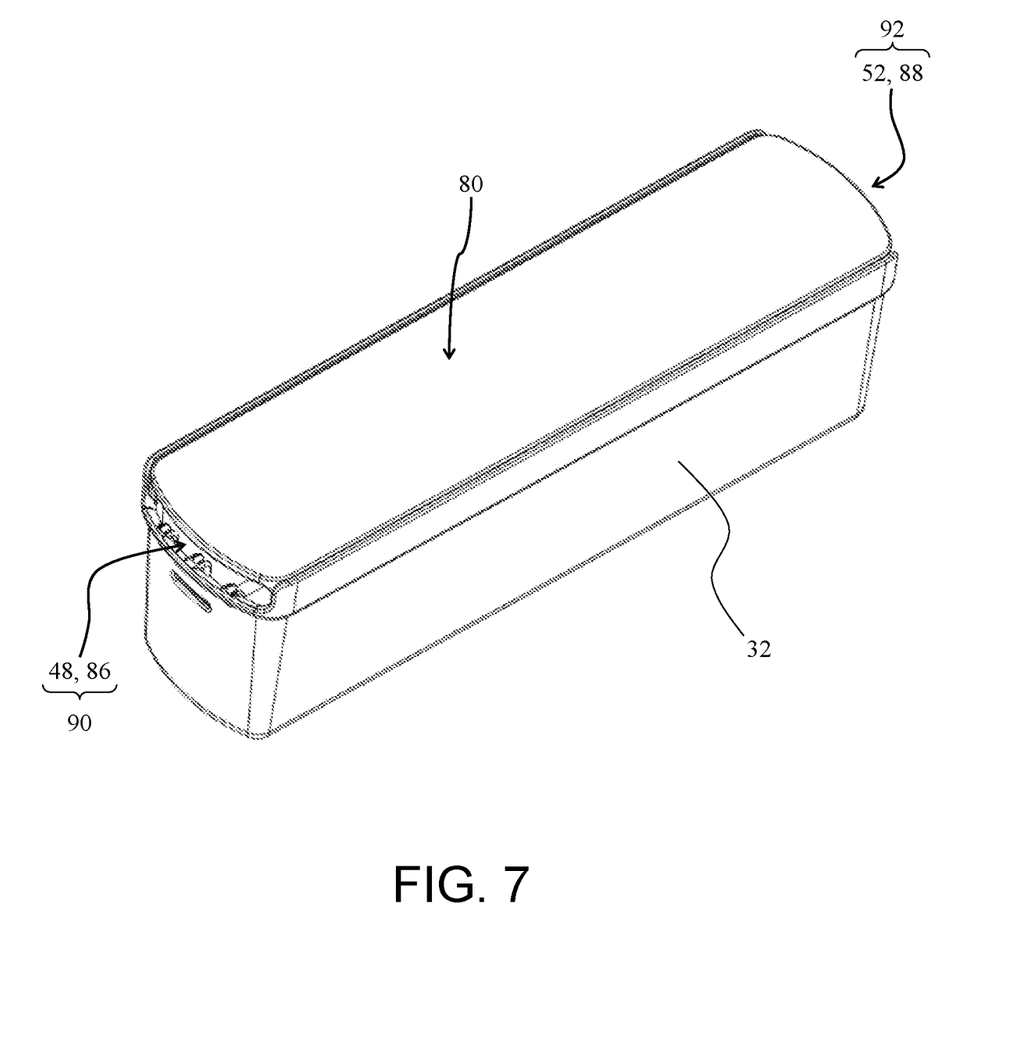
FIG. 7 is a perspective view illustrating the container body to which the lid is attached.

FIG. 7 illustrates the container body 32 to which the lid 80 is attached. By attaching the lid 80 to the container body 32, it is possible to prevent foreign substances, such as dust, from entering the inside of the container body 32. In addition, if the lid 80 is opaque, the probe cable 18 accommodated in the container body 32 is invisible, and thus, the aesthetics of the cable container 30 is improved. Furthermore, the cable container 30 to which the lid 80 is attached can be used as a table on which articles (for example, echo jelly and boxed tissues) can be placed.

When the opening 34 of the container body 32 is blocked by the lid 80, a cable insertion hole 90 that opens forward is formed by the notch 48 of the container body 32 and the notch 86 of the lid 80. The opening of the cable insertion hole 90 has an elongated shape extending in the right-and-left direction. The cable insertion hole 90 is, needless to say, a hole through which the probe cable 18 is inserted.

Figure 8:
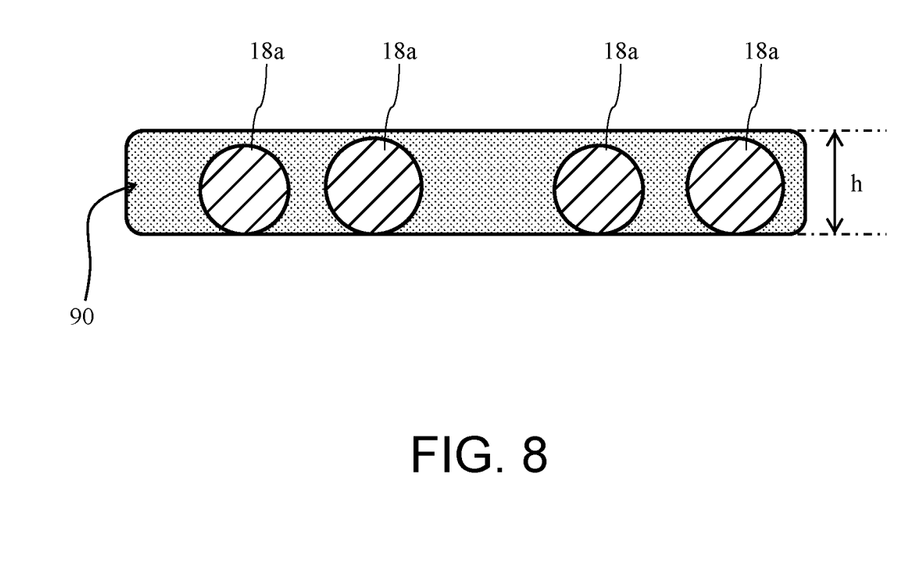
FIG. 8 is a front view of cable insertion holes.

FIG. 8 is a front view of the cable insertion hole 90. The cable insertion hole 90 functions to prevent a plurality of insertion portions 18a of the probe cables 18 inserted through the cable insertion hole 90 from being aligned in the up-and-down direction. More specifically, the height h of the cable insertion hole 90 is designed such that two insertion portions 18a cannot be vertically aligned in the cable insertion hole 90. Here, the insertion portions 18a may be insertion portions 18a of different probe cables 18, or may be two insertion portions 18a of the same probe cable 18. Specifically, the height h of the cable insertion hole 90 is made less than twice the minimum diameter of the probe cable 18 that is expected to be inserted through the cable insertion hole 90. The height h of the cable insertion hole 90 made in such a manner can prevent two insertion portions 18a from being vertically aligned. The height h of the cable insertion hole 90 is naturally made greater than or equal to the maximum diameter among the diameters of the probe cables 18 that are expected to be inserted through the cable insertion hole 90. In the present embodiment, the height h of the cable insertion hole 90 is about 13 mm.

As the cable insertion hole 90 functions as described above, the probe cables 18 are inserted through the cable insertion hole 90 in a row along the right-and-left direction. This prevents or reduces tangling of the probe cables 18 and improves the appearance.

Figure 9:
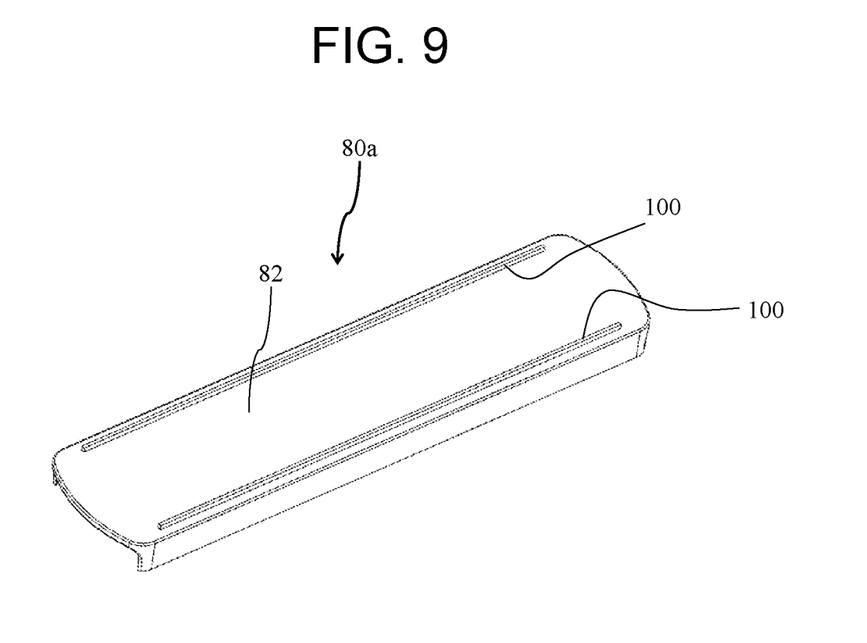
FIG. 9 is a perspective view illustrating a first variant of the lid.

FIG. 9 is a view illustrating a first variant of the lid 80. A lid 80a according to the first variant has ridges 100 arranged along the edges of the upper side surface of the flat plate portion 82. In the present embodiment, the ridges 100 are arranged along both long sides of the flat plate portion 82. The ridge 100 functions to prevent articles placed on the cable container 30, to which the lid 80a is attached, from falling down from the lid 80a. For example, when a cylindrical container of echo jelly is laid on the cable container 30, the ridges 100 prevent the cylindrical container from rolling off from the lid 80a.

Figure 10:
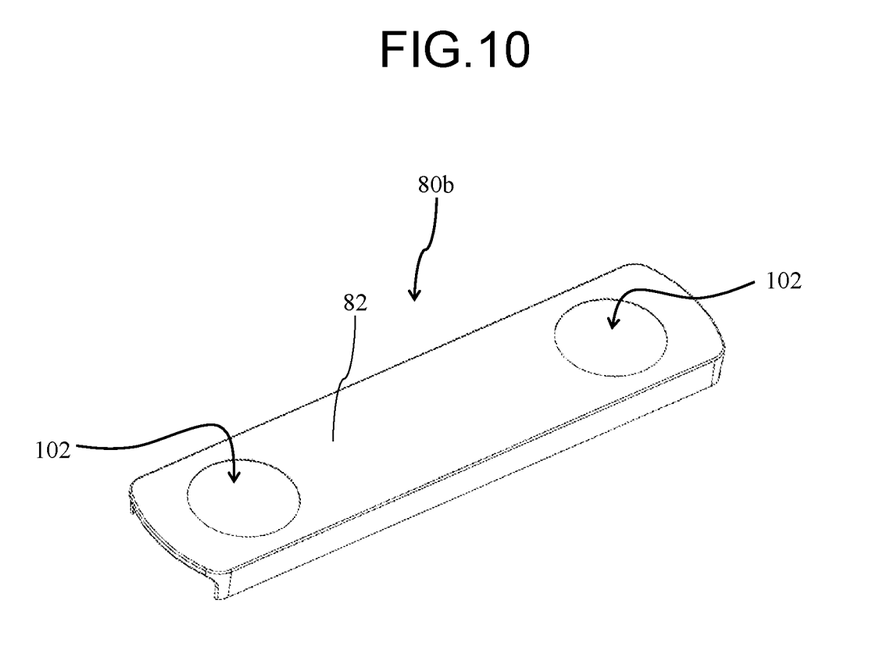
FIG. 10 is a perspective view illustrating a second variant of the lid.

FIG. 10 is a view illustrating a second variant of the lid 80. A lid 80b according to the second variant has, on the upper side surface of the flat plate portion 82, cavities 102 for placing articles therein. In the present embodiment, the shape of the cavity 102 is circular as viewed in a plan view, assuming that an article having a cylindrical shape (for example, a container of echo jelly) is placed therein. The shape of the cavity 102 is, of course, not limited to this. Placing the article in the cavity 102 can make the article less likely to fall over. A plurality of cavities 102 may be provided. In the present embodiment, the lid 80b has two cavities 102.

Figure 11:
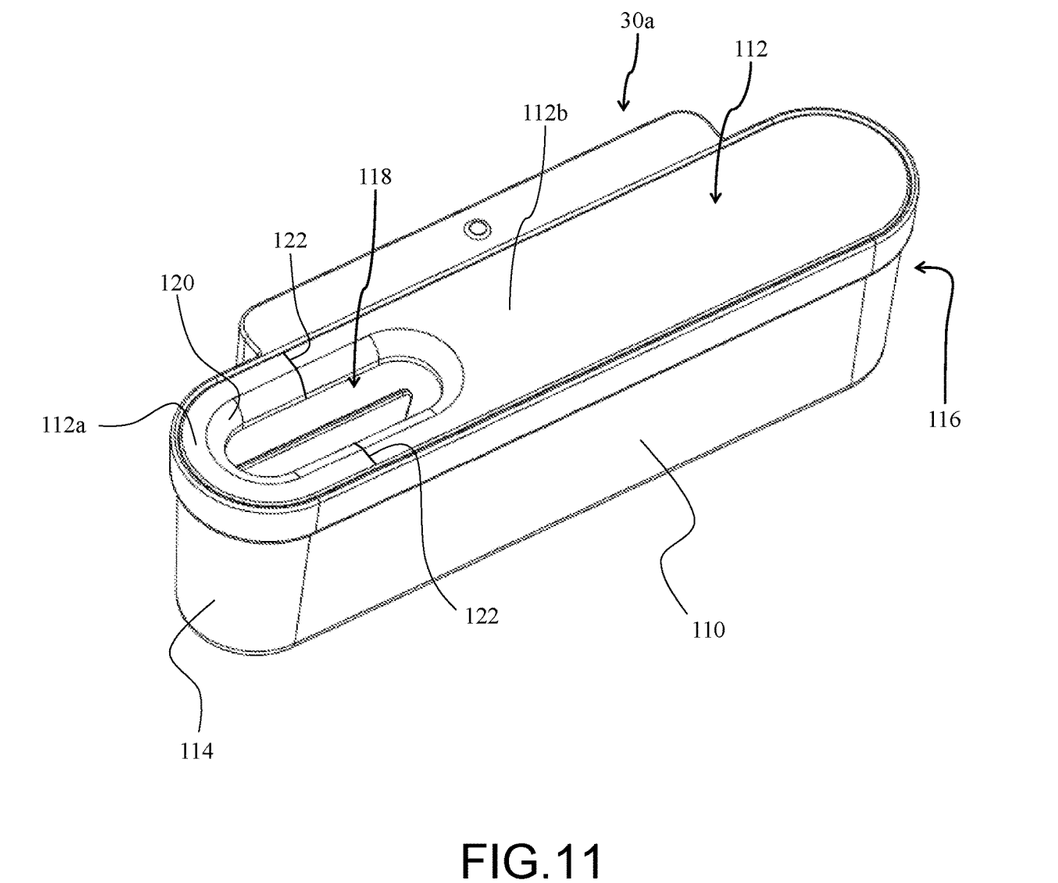
FIG. 11 is a perspective view illustrating a variant of the cable container.

FIG. 11 is a perspective view illustrating a variant of the cable container 30. Like the cable container 30 according to the basic embodiment, a cable container 30a according to the variant is also attached to the right side surface 12b or the left side surface 12c of the device body 12 and accommodates the probe cable 18. The cable container 30a is also configured to include a container body 110 having an opening that opens upward and a lid 112 detachably attached to the opening. However, unlike the cable container 30, the cable container 30a has no notch in a front side wall 114 or a rear side wall 116 of the container body 110.

In the cable container 30a, the lid 112 has a cable insertion hole 118 for inserting the probe cable 18 therethrough. As described above, because the probe connector 20 is connected to the front side surface 12a of the device body 12, and the subject is often positioned in front of the device body 12, it is desirable to provide the cable insertion hole 118 on the front side of the lid 112, in terms of reduction in wiring length of the cable 18 outside the cable container 30a. The lid 112 can also be attached to the container body 110 with the front side back, and thus, when the cable container 30a is attached to the left side surface 12c of the device body 12, the lid 112 can be attached to the container body 110 such that the cable insertion hole 118 is located on the rear side. It is also desirable that an edge of the cable insertion hole 118 be chamfered. In the example in FIG. 11, a gentle slope 120 is formed on the edge of the cable insertion hole 118.

Providing the cable insertion hole 118 in the lid 112; that is, in the upper side surface of the cable container 30a, allows the probe cable 18 to extend upward from the inside of the cable container 30a to the outside. It is thus possible to make the probe cable 18 extending outside less likely to contact the floor surface as compared with the case where the cable insertion hole is provided in the side surface of the cable container 30a.

In order to facilitate accommodation of the probe cable 18 in the cable container 30a, the lid 112 may be separated by a dividing line 122 that traverses the cable insertion hole 118. In the example in FIG. 11, the lid 112 is separable into a front side portion 112a that is on the front side of the dividing line 122 extending in the right-and-left direction and a rear side portion 112b that is on the rear side of the dividing line 122. The operator may put the excess length of the probe cable 18 into the cable container 30a and then assemble the front side portion 112a and the rear side portion 112b in turn while positioning the probe cable 18 so that the probe cable 18 (portion extending outside the cable container 30a) passes through the cable insertion hole 118. This eliminates the necessity of inserting the probe cable 18 into the cable insertion hole 118 from its tip end (that is, the ultrasound probe 14 or the probe connector 20), in order to pass the probe cable 18 through the cable insertion hole 118. In this case, the front side portion 112a or the rear side portion 112b may be attached to the container body 110 in a fixed (undetachable) manner.

Although the embodiments of the ultrasound diagnostic device according to the present disclosure have been described, the ultrasound diagnostic device according to the present disclosure is not limited to the above embodiments, and various changes can be made without departing from the spirit of the present disclosure.

The invention claimed is:

1. An ultrasound diagnostic device, comprising:
    a cable container provided on either one of a right side surface and a left side surface of a device body, for accommodating a probe cable connecting an ultrasound probe and a probe connector, the ultrasound probe transmitting and receiving ultrasound waves to and from a subject, the probe connector being connected to a front side surface of the device body,
    wherein the cable container has a container body including:
    an opening that opens upward,
    a front notch in an upper end of a front side wall of the container body, for passing the probe cable therethrough,
    a rear notch in an upper end of a rear side wall of the container body,
    a left wall having an upper portion extending higher than the front side wall and the rear side wall, and
    a right wall having an upper portion extending higher than the front side wall and the rear side wall,
    wherein the front side wall is sloped outward along a bottom portion of the front notch, and
    wherein the rear side wall is sloped outward along a bottom portion of the rear notch.

2. The ultrasound diagnostic device according to claim 1, wherein respective inside corners of the front notch and the back notch are chamfered.

3. The ultrasound diagnostic device according to claim 1, further comprising:
    a partition extending parallel with the left wall and the right wall; and
    a recess in each of the front side wall and the rear side wall,
    wherein the partition engages with the recesses in the front side wall and the rear side wall.

4. The ultrasound diagnostic device according to claim 1, further comprising a detachable lid that blocks the opening of the container body.

5. The ultrasound diagnostic device according to claim 4, wherein, when the opening is blocked by the lid, a cable insertion hole formed by each notch and the lid functions to prevent a plurality of insertion portions of the probe cables inserted into a respective cable insertion hole from being aligned in the up-and-down direction.

6. The ultrasound diagnostic device according to claim 4, wherein a ridge is provided along an edge of an upper side surface of the lid.

7. The ultrasound diagnostic device according to claim 4, wherein a cavity for placing an article therein is provided on an upper side surface of the lid.

8. An ultrasound diagnostic device, comprising:
    a cable container provided on either one of a right side surface and a left side surface of a device body, for accommodating a probe cable connecting an ultrasound probe and a probe connector, the ultrasound probe transmitting and receiving ultrasound waves to and from a subject, the probe connector being connected to a front side surface of the device body,
    wherein the cable container has a container body including:
    an opening that opens upward,
    a lid that is detachably attached to the opening and is provided with a cable insertion hole for inserting the probe cable therethrough,
    a front notch in an upper end of a front side wall of the container body, for passing the probe cable therethrough,
    a rear notch in an upper end of a rear side wall of the container body,
    a left wall having an upper portion extending higher than the front side wall and the rear side wall, and
    a right wall having an upper portion extending higher than the front side wall and the rear side wall,
    wherein the front side wall is sloped outward along a bottom portion of the front notch, and
    wherein the rear side wall is sloped outward along a bottom portion of the rear notch.

* * * * *